US008808738B2

(12) United States Patent
Bhagat et al.

(10) Patent No.: US 8,808,738 B2
(45) Date of Patent: *Aug. 19, 2014

(54) ALIPHATIC AMINE POLYMER SALTS FOR TABLETING

(75) Inventors: Hitesh R. Bhagat, Wayland, MA (US); Jeffrey M. Goldberg, Framingham, MA (US); Abizer I. Harianawala, Lexington, MA (US); Louis Brenner, Brookline, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/183,079

(22) Filed: Jul. 14, 2011

(65) Prior Publication Data

US 2012/0121704 A1  May 17, 2012

Related U.S. Application Data

(63) Continuation of application No. 11/262,291, filed on Oct. 27, 2005, now Pat. No. 7,985,418.

(60) Provisional application No. 60/624,001, filed on Nov. 1, 2004, provisional application No. 60/628,752, filed on Nov. 17, 2004.

(51) Int. Cl.
  *A61K 9/20* (2006.01)

(52) U.S. Cl.
  USPC .......................................... 424/464

(58) Field of Classification Search
  None
  See application file for complete search history.

(56) References Cited

U.S. PATENT DOCUMENTS

| | | |
|---|---|---|
| 2,456,428 A | 12/1948 | Parker |
| 3,104,205 A | 9/1963 | Hainer et al. |
| 3,308,020 A | 3/1967 | Tennant et al. |
| 3,332,841 A | 7/1967 | Ainsworth et al. |
| 3,383,236 A | 5/1968 | Brindamour |
| 3,431,138 A | 3/1969 | Zingerman et al. |
| 3,539,380 A | 11/1970 | Johnson et al. |
| 3,624,209 A | 11/1971 | Granatek et al. |
| 3,980,770 A | 9/1976 | Ingelman et al. |
| 4,071,478 A | 1/1978 | Shen et al. |
| 4,115,537 A | 9/1978 | Driscoll et al. |
| 4,143,130 A | 3/1979 | Imondi et al. |
| 4,181,718 A | 1/1980 | Mason et al. |
| 4,183,918 A | 1/1980 | Asher et al. |
| 4,205,064 A | 5/1980 | Wagner et al. |
| 4,211,763 A | 7/1980 | Marshall et al. |
| 4,247,393 A | 1/1981 | Wallace |
| 4,264,573 A | 4/1981 | Powell et al. |
| 4,302,440 A | 11/1981 | John et al. |
| 4,341,563 A | 7/1982 | Kurihara et al. |
| 4,344,993 A | 8/1982 | Schmidt et al. |
| 4,504,640 A | 3/1985 | Harada et al. |
| 4,507,466 A | 3/1985 | Tomalia et al. |
| 4,539,198 A | 9/1985 | Powell et al. |
| 4,543,370 A | 9/1985 | Porter et al. |
| 4,605,701 A | 8/1986 | Harada et al. |
| 4,631,305 A | 12/1986 | Guyer et al. |
| 4,762,524 A | 8/1988 | Chambers et al. |
| 4,849,227 A | 7/1989 | Cho |
| 4,871,779 A | 10/1989 | Killat et al. |
| 4,895,621 A | 1/1990 | Hassler |
| 4,956,182 A | 9/1990 | Bequette et al. |
| 4,983,398 A | 1/1991 | Gaylord et al. |
| 4,983,399 A | 1/1991 | Maish |
| 5,053,423 A | 10/1991 | Liu |
| 5,055,197 A | 10/1991 | Albright et al. |
| 5,073,380 A | 12/1991 | Babu et al. |
| 5,108,767 A | 4/1992 | Mulchandani et al. |
| 5,194,464 A | 3/1993 | Itoh et al. |
| 5,262,167 A | 11/1993 | Vegesna et al. |
| 5,302,531 A | 4/1994 | Bauer |
| 5,373,052 A | 12/1994 | Fukuda et al. |
| 5,374,422 A | 12/1994 | St. Pierre et al. |
| 5,401,515 A | 3/1995 | Woodard et al. |
| 5,414,068 A | 5/1995 | Bliem et al. |
| 5,428,112 A | 6/1995 | Ahlers et al. |
| 5,430,110 A | 7/1995 | Ahlers et al. |
| 5,447,726 A | 9/1995 | Nomura |
| 5,455,047 A | 10/1995 | Bequette et al. |

(Continued)

FOREIGN PATENT DOCUMENTS

| | | |
|---|---|---|
| AU | 689797 | 4/1998 |
| CH | 656 535 A5 | 7/1986 |

(Continued)

OTHER PUBLICATIONS

Bhadra, D. et al., "Glycodendrimeric Nanoparticulate Carriers of Primaquine Phosphate for Liver Targeting" International Journal of Pharmaceutics, 295 (Mar. 2005) 221-233.
De Brabander-van den Berg, Ellen M. M. et al., "Poly(propylenimin)-Dendrimere: Synthese in größerem Maβstab durch heterogen katalysierte Hydrierungen" Angew. Chem. (1993) 1370-1372. [in German only].
Duncan, Ruth et al., "Dendrimer biocompatibility and toxicity" Advanced Drug Delivery Reviews, 57 (2005) 2215-2237.
Gao, C., "Hyperbranched polymers made from A2, B2 and BB'2 type monomers, 2. Preparation of hyperbranched copoly(sulfone-amine)s by polyaddition of N-ethylethylenediamine and piperazine to divinylsulfone" Polymer (2001), 42(8), 3437-3443.

(Continued)

*Primary Examiner* — Paul Dickinson
(74) *Attorney, Agent, or Firm* — Jones Day

(57) ABSTRACT

The tablets, compositions and methods of the present invention, comprising a carbonate salt of an aliphatic amine polymer and s monovalent anion can prevent or ameliorate acidosis, in particular acidosis in patients with renal disease. The tablets and compositions of the present invention maintain a disintegration time of no greater than 30 minutes at 37° C. and at pH of at least 1 for a period of at least ten weeks at 60° C. Furthermore, the tablets are stable for extended periods of time without the need for specialized storage conditions.

24 Claims, No Drawings

(56) References Cited

U.S. PATENT DOCUMENTS

| | | |
|---|---|---|
| 5,462,730 A | 10/1995 | McTaggart et al. |
| 5,487,888 A | 1/1996 | Mandeville et al. |
| 5,496,545 A | 3/1996 | Holmes-Farley et al. |
| 5,520,932 A | 5/1996 | McCurdy et al. |
| 5,530,092 A | 6/1996 | Meijer et al. |
| 5,561,214 A | 10/1996 | Yeske et al. |
| 5,607,669 A | 3/1997 | Mandeville, III et al. |
| 5,610,268 A | 3/1997 | Meijer et al. |
| 5,618,530 A | 4/1997 | Mandeville, III et al. |
| 5,624,963 A | 4/1997 | Mandeville, III et al. |
| 5,654,003 A | 8/1997 | Fuisz et al. |
| 5,667,775 A | 9/1997 | Holmes-Farley et al. |
| 5,679,717 A | 10/1997 | Mandeville, III et al. |
| 5,686,106 A | 11/1997 | Kelm et al. |
| 5,693,675 A | 12/1997 | Mandeville, III et al. |
| 5,702,696 A | 12/1997 | Mandeville, III et al. |
| 5,703,188 A | 12/1997 | Mandeville, III et al. |
| 5,709,880 A | 1/1998 | Del Corral et al. |
| 5,718,920 A | 2/1998 | Notenbomer |
| 5,747,067 A | 5/1998 | Auguello et al. |
| 5,750,148 A | 5/1998 | Maruyama et al. |
| 5,807,582 A | 9/1998 | Cha |
| 5,814,336 A | 9/1998 | Kelm et al. |
| 5,840,339 A | 11/1998 | Kunin |
| 5,840,766 A | 11/1998 | Mandeville, III et al. |
| 5,900,475 A | 5/1999 | Mandeville, III et al. |
| 5,919,832 A | 7/1999 | Mandeville, III et al. |
| 5,959,069 A | 9/1999 | Gluck et al. |
| 5,969,090 A | 10/1999 | Mandeville, III et al. |
| 5,985,938 A | 11/1999 | Holmes-Farley et al. |
| 6,022,533 A | 2/2000 | Goto et al. |
| 6,034,129 A | 3/2000 | Mandeville, III et al. |
| 6,037,444 A | 3/2000 | Rannard et al. |
| 6,083,495 A | 7/2000 | Holmes-Farley et al. |
| 6,083,497 A | 7/2000 | Huval et al. |
| 6,090,411 A | 7/2000 | Pillay et al. |
| 6,177,478 B1 | 1/2001 | Holmes-Farley et al. |
| 6,180,754 B1 | 1/2001 | Stutts et al. |
| 6,187,897 B1 | 2/2001 | Kawashima et al. |
| 6,190,650 B1 | 2/2001 | Matthews et al. |
| 6,203,785 B1 | 3/2001 | Holmes-Farley et al. |
| 6,248,318 B1 | 6/2001 | Huval et al. |
| 6,264,937 B1 | 7/2001 | Mandeville, III et al. |
| 6,274,713 B1 | 8/2001 | Sieving et al. |
| 6,281,252 B1 | 8/2001 | Holmes-Farley et al. |
| 6,284,275 B1 | 9/2001 | Chen |
| 6,335,402 B1 | 1/2002 | Mihan et al. |
| 6,362,266 B1 | 3/2002 | Buchholz et al. |
| 6,383,518 B1 | 5/2002 | Matsuda et al. |
| 6,423,754 B1 | 7/2002 | Holmes-Farley et al. |
| 6,509,013 B1 | 1/2003 | Holmes-Farley et al. |
| 6,534,600 B2 | 3/2003 | Dvornic et al. |
| 6,566,407 B2 | 5/2003 | Holmes-Farley et al. |
| 6,600,011 B2 | 7/2003 | McDonnell et al. |
| 6,605,270 B1 | 8/2003 | Mandeville et al. |
| 6,696,087 B2 | 2/2004 | Matsuda et al. |
| 6,726,905 B1 | 4/2004 | Mandeville, III et al. |
| 6,733,780 B1 | 5/2004 | Tyler et al. |
| 6,844,372 B2 | 1/2005 | Goto et al. |
| 6,858,203 B2 | 2/2005 | Holmes-Farley et al. |
| 6,908,609 B2 | 6/2005 | Simon et al. |
| 7,014,846 B2 | 3/2006 | Holmes-Farley et al. |
| 7,019,085 B2 | 3/2006 | Albright |
| 7,081,509 B2 | 7/2006 | Wagner et al. |
| 7,087,223 B2 | 8/2006 | Goto et al. |
| 7,101,960 B2 | 9/2006 | Mandeville, III et al. |
| 7,220,406 B2 | 5/2007 | Burke |
| 7,335,795 B2 | 2/2008 | Chang et al. |
| 7,342,083 B2 | 3/2008 | Chang et al. |
| 7,385,012 B2 | 6/2008 | Chang et al. |
| 7,449,605 B2 | 11/2008 | Chang et al. |
| 7,459,151 B2 | 12/2008 | Holmes-Farley et al. |
| 7,459,502 B2 | 12/2008 | Connor et al. |
| 7,589,238 B2 | 9/2009 | Connor et al. |
| 2002/0054903 A1 | 5/2002 | Tyler et al. |
| 2002/0114774 A1 | 8/2002 | Fitzpatrick et al. |
| 2002/0122786 A1 | 9/2002 | Matsuda et al. |
| 2002/0159968 A1 | 10/2002 | Petersen et al. |
| 2002/0160050 A1 | 10/2002 | Elema et al. |
| 2002/0168333 A1 | 11/2002 | Burke |
| 2002/0182168 A1 | 12/2002 | Holmes-Farley et al. |
| 2002/0187120 A1 | 12/2002 | Holmes-Farley et al. |
| 2002/0187121 A1 | 12/2002 | Burke |
| 2003/0039627 A1 | 2/2003 | Holmes-Farley et al. |
| 2003/0049226 A1* | 3/2003 | Burke et al. ............... 424/78.35 |
| 2003/0086898 A1 | 5/2003 | Holmes-Farley et al. |
| 2003/0133902 A1 | 7/2003 | Holmes-Farley et al. |
| 2003/0161875 A1 | 8/2003 | Murpani et al. |
| 2003/0175349 A1 | 9/2003 | Garg et al. |
| 2003/0180250 A1 | 9/2003 | Chauhan et al. |
| 2003/0199090 A1 | 10/2003 | Monahan et al. |
| 2004/0019020 A1 | 1/2004 | Jozefiak et al. |
| 2004/0022844 A1 | 2/2004 | Hasenzahl et al. |
| 2004/0170695 A1 | 9/2004 | Elama et al. |
| 2004/0185111 A1 | 9/2004 | Rubino et al. |
| 2004/0191209 A1 | 9/2004 | Oba |
| 2004/0191212 A1 | 9/2004 | Holmes-Farley et al. |
| 2005/0084476 A1 | 4/2005 | Goto et al. |
| 2005/0096438 A1 | 5/2005 | Chang et al. |
| 2005/0123614 A1 | 6/2005 | Kim et al. |
| 2005/0131138 A1 | 6/2005 | Connor et al. |
| 2005/0131161 A1 | 6/2005 | Mandeville, III et al. |
| 2005/0147580 A1 | 7/2005 | Connor et al. |
| 2005/0165190 A1 | 7/2005 | Chang et al. |
| 2005/0208095 A1 | 9/2005 | Hunter et al. |
| 2005/0209423 A1 | 9/2005 | Chang et al. |
| 2005/0220752 A1 | 10/2005 | Charmot et al. |
| 2005/0220889 A1 | 10/2005 | Charmot et al. |
| 2005/0220890 A1 | 10/2005 | Charmot et al. |
| 2005/0239901 A1 | 10/2005 | Chang et al. |
| 2005/0260236 A1 | 11/2005 | Tyler et al. |
| 2005/0282010 A1 | 12/2005 | Xu |
| 2006/0024336 A1 | 2/2006 | Charmot et al. |
| 2006/0029663 A1 | 2/2006 | Uchida et al. |
| 2006/0034914 A1 | 2/2006 | Tyler et al. |
| 2006/0043984 A1 | 3/2006 | Miller et al. |
| 2006/0047086 A1 | 3/2006 | Albright et al. |
| 2006/0054914 A1 | 3/2006 | Hsian Yi |
| 2006/0088592 A1 | 4/2006 | Choi et al. |
| 2006/0116391 A1* | 6/2006 | Horbury et al. ............... 514/275 |
| 2006/0134225 A1 | 6/2006 | Moerck et al. |
| 2006/0171916 A1 | 8/2006 | Holmes-Farley et al. |
| 2006/0177415 A1 | 8/2006 | Burke |
| 2006/0239959 A1 | 10/2006 | Holmes-Farley et al. |
| 2006/0251614 A1 | 11/2006 | Bhagat et al. |
| 2006/0258812 A1 | 11/2006 | Gopalkrishna et al. |
| 2006/0292192 A1 | 12/2006 | Hasenzahl et al. |
| 2007/0035313 A1 | 2/2007 | Wuersch et al. |
| 2007/0059277 A1 | 3/2007 | Bhagat et al. |
| 2007/0071715 A1 | 3/2007 | DeLuca et al. |
| 2007/0094779 A1 | 5/2007 | Dauphin |
| 2007/0098678 A1 | 5/2007 | Bhagat et al. |
| 2007/0110707 A1 | 5/2007 | Ravi |
| 2007/0155950 A1 | 7/2007 | Mandeville, III et al. |
| 2007/0224283 A1 | 9/2007 | Chang et al. |
| 2008/0107737 A1 | 5/2008 | Chang et al. |
| 2008/0226735 A1 | 9/2008 | Moerck et al. |
| 2008/0292697 A1 | 11/2008 | Tyler et al. |

FOREIGN PATENT DOCUMENTS

| | | |
|---|---|---|
| CN | 1290515 | 12/2006 |
| DE | 4010271 | 10/1991 |
| EP | 0162388 A1 | 11/1985 |
| EP | 0375350 A2 | 6/1990 |
| EP | 0379161 A2 | 7/1990 |
| EP | 0449151 A2 | 10/1991 |
| EP | 0534304 A1 | 3/1993 |
| EP | 0605757 A1 | 7/1994 |
| EP | 0737759 | 10/1996 |
| EP | 0997148 | 5/2000 |
| EP | 1153940 | 11/2001 |
| EP | 1682606 | 7/2006 |
| EP | 1687349 | 8/2006 |

(56) References Cited

FOREIGN PATENT DOCUMENTS

| | | |
|---|---|---|
| EP | 1742613 | 1/2007 |
| EP | 0211991 | 3/2007 |
| EP | 1831266 | 9/2007 |
| FR | 2217010 A | 9/1974 |
| FR | 2232563 | 1/1975 |
| GB | 929391 | 6/1963 |
| GB | 1238597 A | 7/1971 |
| GB | 2036048 A | 11/1978 |
| GB | 2391730 | 12/1978 |
| GB | 1573487 | 8/1980 |
| GB | 2090605 | 7/1982 |
| GB | 2276170 | 9/1994 |
| GB | 2169356 | 7/2000 |
| JP | 50-34095 | 2/1975 |
| JP | 58079022 | 5/1983 |
| JP | 60152424 A | 8/1985 |
| JP | 62-132830 | 6/1987 |
| JP | 4-503962 | 3/1990 |
| JP | 5-244915 | 9/1993 |
| JP | 6-321786 | 11/1994 |
| JP | 10316576 A | 12/1998 |
| JP | 2000178182 A | 6/2000 |
| NL | 7401543 | 8/1974 |
| NL | 7603653 | 10/1976 |
| RU | 1808015 A3 | 4/1993 |
| WO | WO 90/02148 | 3/1990 |
| WO | WO 92/10522 | 6/1992 |
| WO | WO 93/00915 | 1/1993 |
| WO | WO 93/05793 | 1/1993 |
| WO | WO 94/19379 | 1/1994 |
| WO | WO 94/04596 | 3/1994 |
| WO | WO 94/27620 | 12/1994 |
| WO | WO 94/27621 | 12/1994 |
| WO | WO 95/05184 | 2/1995 |
| WO | WO 96/21454 | 7/1996 |
| WO | WO 96/25440 | 8/1996 |
| WO | WO 96/39156 | 12/1996 |
| WO | WO 97/49771 | 12/1997 |
| WO | WO 98/29107 | 7/1998 |
| WO | WO 98/42355 | 10/1998 |
| WO | WO 98/44933 | 10/1998 |
| WO | WO 99/22721 | 5/1999 |
| WO | WO 99/22743 | 5/1999 |
| WO | WO 00/22008 | 4/2000 |
| WO | WO 01/28527 | 4/2001 |
| WO | WO 02/085378 | 10/2002 |
| WO | WO 2004/037274 | 5/2004 |
| WO | WO 2004/099288 | 11/2004 |
| WO | WO 2005/021000 | 3/2005 |
| WO | WO 2005/041900 | 5/2005 |
| WO | WO 2005/041902 | 5/2005 |
| WO | WO 2005/092039 | 10/2005 |
| WO | WO 2006/043984 | 4/2006 |
| WO | WO 2006/050314 | 5/2006 |

OTHER PUBLICATIONS

Gao, C., "Preparation of Water Soluble hyperbranched poly(sulfone-amine)s by polyaddition of N-ethylethylenediamine to divinyl sulfone" Polymer (2001), 42(18), 7603-7610.

Gao, Chao, "Hyperbranched copolymers made from A2, B2 and BB'2 type monomers (iv). Copolymerization of divinyl sulfone with 4,4'-trimethylenedipiperidine and N-ethylethylenediamine" Science in China, Series B: Chemistry (2001), 44(2), 207-215.

Gao, Chao, "Hyperbranched copolymers made from A2, B2 and BB'2 type monomers, 3a: comparison of copoly(sulfone-amine)s containing piperazine and 4,4'-trimethylenedipiperidine units" Macromolecular Chemistry and Physics (2001), 202(15), 3035-3042.

Gao, Chao, "Hyperbranched polymers made from A2- and BB'-type monomers; 3. Polyaddition of N-methyl 1,3-propanediamine to divinyl sulfone" Macromolecular Chemistry and Physics (2001), 202(12), 2623-2629.

Gao, Chao, "Polyaddition of B2 and BB'2 Type Monomers to A2 Type Monomer. 1. Synthesis of Highly Branched Copoly(sulfonamine)s" Macromolecules (2001), 34(2), 156-161.

Gao, Chao, "Synthesis of hyperbranched polymers from commercially available A2 and BB'2 type monomers" Chemical Communications (Cambridge), 1 (2001) 107-108.

Hobson, Lois J., et al. "Poly(amidoamine) Hyperbranched Systems:Synthesis, Structure and Characterization" Polymer, 40 (1999) 1279-1297.

Huval, Chad C. et al., "Syntheses of hydrophobically modified cationic hydrogels by copolymerization of alkyl substituted diallylamine monomers and their use as bile acid sequestrants" European Polymer Journal, 40 (2004) 693-701.

Jansen, Johan F.G.A. et al. "The Dendritic Box: Shape-Selective Liberation of Encapsulated Guests" J. Am. Chem. Soc., 117 (1995) 4417-4418.

Janssen, H.M. et al, "The Synthesis and Characterization of Dendritic Molecules" Eindhoven University of Technology [No date available].

Jayamurugan, Govindasamy, et al., "Synthesis of Large Generation poly(propul ether imine) (PETIM) Dendrimers" Tetrahedron, 62 (2006) 9582-9588.

Klapper, Marcus et al., "Poly(methylene amine): A Polymer with the Maximum Possible Number of Amino Groups on a Polymer Backbone" Angew. Chem. Int. Ed., 42 (2003) 4687-4690 (XP002456407).

Koç, Fikret, et al. "Highly Regioselective Synthesis pf Amino-Functionalized Dendritic PolyGlycerols by a One Pot Hydroformylation/Reductive Amination Sequence" J. Org. Chem., 70 (2005) 2021-2025.

Kremer, Michael, et al., "Pore-Size Distributions of Cationic Polyacrylamide Hydrogels Varying in Initial Monomer Concentration and Crosslnker/Monomer Ratio" Macromolecules, 27 (1994) 2965-2973.

Kuga, Shigenori, "Pore Size Ditribution Analysis of Gel Substances by Size Exclusion Chromatography" J. Chromatography, 206 (1981) 449-461.

Maroni, Bradley J. et al. "Renal Bioreplacement Therapy is Associated with a Reduction in Mortality in Patients with Acute Renal Failure: Results of a Randomized, Multi-Center, Phase II Trial" ERA-EDTA: Abstract #551794 (2006).

Mourey, T. H., et al., "Unique Behavior of Dendritic Molecules: Intrinsic Viscosity of Polyether Dendrimers" Macromolecules, 25 (1992) 2401-2406.

Newkome, George R. et al., "Improved Synthesis of an Ethereal Tetraamine Core for Dendrimer Construction" J. Org. Chem., 67 (2002) 3957-3960.

Pavlov, G. M. et al. "Molecular Characteristics of Poly(propylene imine) Dendrimers as Studied with Translational Diffusion and Viscometry" Colloid. Polym. Sci., 280 (2002) 416-423.

Pérignon, Nelly et al., "Formation and Stabilization in Water of Metal Nanoparticles by a Hyperbranched Polymer Chemically Analgous to PAMAM Dendrimers " Chem Mater., 16 (2004) 4856-4858.

"Renvela: sevelamer carbonate" Prescribing Information, Genzyme Corporation, Nov. 2007.

Rosenbaum, Holmes-Farley, Mandeville, Pitruzzello, Goldberg, "Effect of RenaGel, a non-absorbable, cross-linked, polymeric phosphate binder, on urinary phosphorus excretion in rats" Nephrology Dialysis Transplantation, vol. 12 (1997) 961-964.

Schatzlein, Andreas G. et al., "Preferential liver gene expression with polypropylenimine dendrimers" Journal of Controlled Release, 101 (2005) 247-258.

Shao, Lu et al., "Transport properties of cross-linked polyimide membranes induced by different generations of diaminobutane (DAB) dendrimers" Journal of Membrane Science, 238 (2004) 153-163.

Stasko, Nathan A. et al., "Dendrimers as a Scaffold for Nitric Oxide Release" J. Am. Chem. Soc., 128 (2006) 8265-8271.

Xiao, Youchang et al., "Effects of Thermal Treatments and Dendrimers Chemical Structures on the Properties of Highly Surface Cross-Linked Polyimide Films" Ind. Eng. Chem. Res., 44 (2005) 3059-3067.

(56) References Cited

OTHER PUBLICATIONS

Xiuru Li, et al., "Synthesis and Characterization of Hyperbranched Poly(ester amide)s from Commercially Available Dicarboxylic Acids and Multihydroxyl Primary Amines" Macromolecules, 39 (2006) 7889-7899.

Yan, Deyue, "Hyperbranched Polymers Made from A2 and BB'2 Type Monomers. 1. Polyaddition of 1-(2-Aminoethyl)piperazine to Divinyl Sulfone" Macromolecules (2000), 33(21), 7693-7699.

Burt, Helen et al., "Ion-Exchange Resins as Potential Phosphate-Binding Agents for Renal Failure Patients: Effect of the Physiochemical Properties of Resins on Phosphate and Bile Salt Binding," Journal of Pharmaceutical Sciences, vol. 76, No. 5 (May 1987) pp. 379-383.

Delmez, James A. et al., "Hyperphosphatemia: Its Consequences and Treatment in Patients with Chronic Renal Disease," American Journal of Kidney Diseases, vol. XIX, No. 4 (1992) pp. 303-317.

Emmett, Michael et al., "Calcium Acetate Control of Serum Phosphorus in Hemodialysis Patients," American Journal of Kidney Diseases, vol. XVII, No. 5 (1991) pp. 544-550.

Ghosh, J.P. et al., "Preparation and Properties of a New Chelating Resin Containing 2-Nitroso-1-naphthol," Talanta, vol. 28 (1981) pp. 957-959.

Mai, Martin L. et al., "Calcium acetate, an effective phosphorus binder in patients with renal failure," Kidney International, vol. 36 (1989) pp. 690-695.

McGary, T.J. et al., "Polycation as an Alternative Osmotic Agent and Phosphate Binder in Peritoneal Dialysis," Uremia Investigation, vol. 8, No. 2 (1984-1985) pp. 79-84.

Munson, Paul L., "Studies on the Role of the Parathyroids in Calcium and Phosphorus Metabolism," Annals New York Academy of Sciences (Jun. 1993) pp. 776-795.

Petrariu, I. et al., "Hofmann degradation in quaternary basic ammonium polymers: I. Degradation of the linear and crosslined basic benzylic polyelectrolytes in alkaline media," Majer. Plast. (Bucharest), vol. 9, No. 9 (1972) pp. 467-472.

Physicians' Desk Reference, Consult 1992 Supplements for Revisions—"PhosLo® Calcium Acetate Tablets".

Physicians' Desk Reference, Consult 1992 Supplements for Revisions—"Amphojel® Suspension Tablets", p. 2429.

Proceedings of the American Chemical Society Division of Polymeric Materials: Science and Engineering, Boston, Massachusetts, vol. 62 (1990) pp. 259-263.

Salusky, I.B. et al., "Aluminum Accumulation During Treatment with Aluminum Hydroxide and Dialysis in Children and Young Adults with Chronic Renal Disease," The New England Journal of Medicine, vol. 324, No. 8 (1991) pp. 527-531.

Shkinev, V.M. et al., "Anion exchange extraction and enrichment from aqueous solutions by quaternary ammonium reagents," Solvent Extraction and Ion Exchange, vol. 7, No. 3 (1989) pp. 499-510.

Slatopolsky, Eduardo et al., "Calcium Carbonate as a Phosphate Binder in Patients with Chronic Renal Failure Undergoing Dialysis," The New England Journal of Medicine, vol. 315, No. 3 (1986) pp. 157-161.

Ullmanns Encyklopädie der technischen Chemie—Band 19: Polyolefine (1980) pp. 167-178.

Warshawsky, A., "Ion Exchange and Sorption Processes in Hydrometallurgy", Critical Reports on Applied Chemistry, vol. 19: Chapter 4: Chelating Ion Exchangers, M. Streat & D. Naden (Eds.), John Wiley & Sons (1987) pp. 166-225.

Winston, Anthony and Kirchner, Darrell, "Hydroxamic Acid Polymers. Effect of Structure of the Selective Chelation of Iron in Water," Macromolecules, vol. 11, No. 3 (1978) pp. 597-603.

Winston, Anthony and McLaughline, Glenn R., "Hydroxamic Acid Polymers. II. Design of a Polymeric Chelating Agent for Iron," Journal of Polymer Science, vol. 14 (1976) pp. 2155-2165.

Zabutaya, F.I., et al., "Proton NMR spectroscopic study of the reaction of epichlorahydrin with allyamine," Uzb. Chim. Zh., vol. 3 (1984) pp. 23-27. (English Abstract, see XP 002025287).

International Search Report dated Apr. 27, 2006 for PCT/US2005/039366.

Written Opinion dated Apr. 27, 2006 for PCT/US2005/039366.

Physicians Desk Reference "Renagel", 2012.

http://www.answers.com/topic/ions-and-ionization (accessed Aug. 10, 2008).

http://www.rxlist.com/cgi/generic/sevel.htm, accessed Nov. 3, 2007.

Caramella, Carla et al. "Experimental Evidence of Disintegration Mechanisms" Acta Pharm. Technol., 35:1 (1989) 30-33.

Chertow, Glenn M. et al. "The Effects of Sevelamer and Calcium Acetate on Proxies of Atherosclerotic and Arteriosclerotic Vascular Disease in Hemodialysis Patients" Am. J. Nephrol., 23:5 (2003) 307-314.

Ferrari, F. et al. "Investigation on Bonding and Distintegration Properties of Pharmaceutical Materials" International Journal of Pharmaceutics, 136 (1996) 71-79.

Hammouda, Y. et al. "The Use of Sodium Chloride as a Directly Compressible Filler in Therapeutic Tablets" Pharm. Ind., 37:5 (1975) 361-363.

Katopodis, K. P. et al. "Effectiveness of Aluminum Hydroxide Timing Administration in Relation to Meals in Controlling Hyperphosphatemia in Dialysis Patients" The International Journal of Artificial Organs, 28:8 (2005) 803-807.

Lin, Shan-Yang et al. "Influence of Excipients, Drugs, and Osmotic Agent in the Inner Core on the Time-Controlled Disintegration of Compression-Coated Ethylcellulose Tablets" Journal of Pharmaceutical Sciences, 91:9 (Sep. 2002) 2040-2046.

Mattsson, S. et al. "Formulation of High Tensile Strength Rapidly Disintegrating Tablets Evaluation of the Effect of Some Binder Properties" S.T.P. Pharma Sciences, 11:3 (2001) 211-220.

Mitchell, Karen et al. "The Influence of Additives on the Cloud Point, Disintegration and Dissolution of Hydroxypropylmethylcellulose Gels and Matrix Tablets" International Journal of Pharmaceutics, 66 (1990) 233-242.

Schulz, W. "Brief Evaluation: Sevelamer Hydrochloride" Drug, Therapy Criticism, Hans Marseille Publishers GmbH, Munich, Issue 3 (2001) 621-626.

Selmeczi, B. et al. "Investigations of the Influence of Some Novel Auxiliary Agents on the Physical Properties of Tablets" Pharmaceutical Technological Institute of the Medical University of Szeged (Hungary), [No date available].

Soltero, Richard et al. "The Effects of PH. Ionic Concentration and Ionic Species of Dissolution Media on the Release Rates of Quinidine Gluconate Sustained Release Dosage Forms" Drug Development and Industrial Pharmacy, 17:1 (1991) 113-140.

Tirkkonen, Sirpa et al. "Enhancement of Drug Release from Ethylcellulose Microcapsules Using Solid Sodium Chloride in the Wall" International Journal of Pharmaceutics, 88 (1992) 39-51.

Tirkkonen, Sirpa et al. "Release of Indomethacin from Tabletted Ethylcellulose Microcapsules" International Journal of Pharmaceutics, 92 (1993) 55-62.

\* cited by examiner

ALIPHATIC AMINE POLYMER SALTS FOR TABLETING

RELATED APPLICATION

This application is a continuation of U.S. application Ser. No. 11/262,291, filed Oct. 27, 2005, now U.S. Pat. No. 7,985,418, which claims the benefit of both U.S. Provisional Application No. 60/624,001, filed on Nov. 1, 2004, and U.S. Provisional Application No. 60/628,752, filed on Nov. 17, 2004. The foregoing related applications, in their entirety, are incorporated herein by reference.

BACKGROUND OF THE INVENTION

Hyperphosphatemia frequently accompanies diseases associated with inadequate renal function, hyperparathyroidism, and certain other medical conditions. Hyperphosphatemia is typically defined for humans as a serum phosphate level of greater than about 4.5 mg/dL. The condition, especially if present over extended periods of time, leads to severe abnormalities in calcium and phosphorus metabolism and can be manifested by aberrant calcification in joints, lungs and eyes.

Anion exchange polymers, such as aliphatic amine polymers, have been used in the treatment of hyperphosphatemia. These polymers provide an effective treatment for decreasing the serum level of phosphate, without concomitantly increasing the absorption of any clinically undesirable materials.

Metabolic acidosis is another condition which accompanies diseases associated with inadequate renal function. The human body is constantly gaining $H^+$ ions from the metabolism of sugars, fats, protein and lactic acid (produced under anaerobic metabolism). To maintain a constant pH the body must excrete $H^+$ ions. Decreased excretion of $H^+$ ions occurs in patients suffering from renal disease or renal failure, which results in metabolic acidosis and, hence, a low blood pH due to excess $H^+$ ions.

Current treatments for hyperphosphatemia do not address the issue of metabolic acidosis. The present inventors have prepared carbonate salts of aliphatic amine polymers for this purpose, however, tablets made from carbonate salts of aliphatic amine polymers suffer from short shelf life. Further, the disintegration time of tablets made from carbonate salts increases over time when stored under standard storage conditions. This increase in disintegration time may lead to decreased availability of the active components of the drug to a patient.

SUMMARY OF THE INVENTION

It has now been found that adding a monovalent anion source to tablets of aliphatic amine carbonates salts significantly increases the shelf life, and prevents the disintegration time from increasing over time when the tablets are stored under standard storage conditions. Further it has been found that increasing the particle size of the aliphatic amine polymer particles in the tablets significantly increases the shelf life, and prevents the disintegration time from increasing over time when the tablets are stored under standard storage conditions.

In one embodiment, the present invention is a tablet comprising a carbonate, bicarbonate, acetate or lactate salt of an aliphatic amine polymer, wherein said tablet maintains a disintegration time of no greater than 30 minutes at 37° C. and at a pH of at least 1 when stored for a period of at least ten weeks at 60° C. Preferably the aliphatic amine polymer is sevelamer.

In another embodiment the present invention is a tablet comprising a carbonate, bicarbonate, acetate or lactate salt of an aliphatic amine polymer and a monovalent anion source, wherein the monovalent anion comprises at least 0.05% by weight of the combined weights of the carbonate salt and the monovalent anion source.

In another embodiment, the present invention is a composition comprising a carbonate, bicarbonate, acetate or lactate salt of an aliphatic amine polymer and a monovalent anion source, wherein the monovalent anion comprises at least 0.05% by weight of the combined weight of the carbonate salt and the monovalent anion source. Preferably the composition is for pharmaceutical use and additionally comprises a pharmaceutically acceptable carrier or diluent.

In another embodiment the present invention is a tablet comprising sevelamer carbonate particles, wherein at least 95% by volume of the particles have a diameter of at least 45 microns.

In one embodiment the present invention is a method of removing phosphate from a patient in need of such treatment, comprising administering to the patient a therapeutically effective amount of a tablet, composition or pharmaceutical composition disclosed herein.

The tablets, compositions and methods of the present invention, can prevent or ameliorate acidosis, in particular acidosis in patients with renal disease. The disintegration time of the tablets and compositions of the present invention does not increase over time when stored under standard conditions. Furthermore, the tablets are stable for extended periods of time without the need for specialized storage conditions.

DETAILED DESCRIPTION OF THE INVENTION

Current treatments for hyperphosphatemia do not address the issues of low blood pH which often accompanies renal failure. The use of carbonate salts of aliphatic amine polymers would be useful in addressing this issue, however, tablets of carbonate salts often suffer from short shelf lives and disintegration times which increase over time under standard storage conditions. It has now been discovered that adding a monovalent anion source to the carbonate salt prevents the increase in the disintegration time of the tablets and increases the shelf life. It has also been discovered that increasing the particle size of the aliphatic amine polymer prevents the increase in the disintegration time of the tablets and increases the shelf life.

In one embodiment the present invention is a tablet comprising a carbonate, bicarbonate, acetate or lactate salt of an aliphatic amine polymer, wherein said tablet maintains a disintegration time of no greater than 60 minutes, 45 minutes, 30 minutes, preferably 20 minutes, more preferably 15 minutes, most preferably 10 minutes at 37±2° C. The disclosed tablets exhibit these disintegration times over a wide variety of pH ranges including acidic conditions such as a pH of at least 1, more preferably at a pH range of 1-5, preferably 1-4, more preferably 1-3, most preferably 1-2, even more preferably at pH 1.2. The disintegration time can be measured using the procedures described in the United States Pharmacopoeia 27—National Formulary 22 (USP 27—NF 22) which have been adapted according to Example 1. In a preferred embodiment the disintegration time of the tablets remains constant for a period of at least 1 week, 2 weeks, 1 month, 5 weeks, 2 months, 10 weeks, 3 months, 6 months, 1 year, or two years at 60° C. when stored in a sealed, water impervious container. It is to be understood when speaking herein of carbonate salts Applicants' are also referring to bicarbonate, acetate, and lactate salts.

Amine polymers are characterized by a repeat unit that includes at least one amino group. Amino groups can be part of the polymer backbone (e.g., a polyalkyleneimine such as polyethyleneimine), pendant from the polymer backbone (e.g., polyallylamine), or both types of amino groups can exist within the same repeat unit and/or polymer. Amine polymers include aliphatic amine polymers and aromatic amine polymers.

An aliphatic amine polymer is obtained by polymerizing an aliphatic amine monomer. An aliphatic amine is saturated or unsaturated, straight-chained, branched or cyclic non-aromatic hydrocarbon having an amino substituent and optionally one or more additional substituents. An aliphatic amine monomer is an aliphatic amine comprising a polymerizable group such as an olefin. Examples of aliphatic amine polymers include polymers characterized by one or more repeat units set forth below:

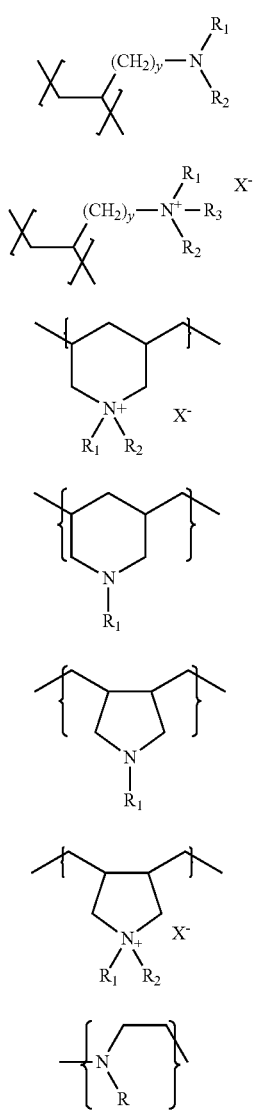

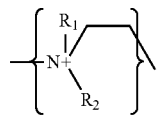

wherein y is an integer of zero, one or more (e.g., between about 1 and 10, 1 and 6, 1 and 4 or 1 and 3) and each R, $R_1$, $R_2$, and $R_3$, independently, is H or a substituted or unsubstituted alkyl group (e.g., having between 1 and 25, preferably between 1 and 5 carbon atoms, such as aminoalkyl having e.g., between 1 and 5 carbons atoms, inclusive, such as aminoethyl or poly(aminoethyl)) or substituted or unsubstituted aryl (e.g., phenyl) group, and each $X^-$ is independently an exchangeable negatively charged counterion. Typically, R, $R_1$, $R_2$, and $R_3$ are each independently H or a substituted or unsubstituted alkyl group.

In one preferred polymer used in the invention, at least one of the R, $R_1$, $R_2$, or $R_3$ groups is a hydrogen atom. In a more preferred embodiment, each of these groups are hydrogen. In one embodiment, R, $R_1$, $R_2$, and $R_3$ are H and the polymer comprises repeat units characterized by Structural Formulas I-IV, VII and/or VIII.

As an alkyl, or aryl group, R, $R_1$, $R_2$, or $R_3$ can carry one or more substituents. Suitable substituents include cationic groups, e.g., quaternary ammonium groups, or amine groups, e.g., primary, secondary or tertiary alkyl or aryl amines. Examples of other suitable substituents include hydroxy, alkoxy, carboxamide, sulfonamide, halogen, alkyl, aryl, hydrazine, guanadine, urea, poly(alkyleneimine), such as poly(ethyleneimine), and carboxylic acid esters.

One example of a preferred aliphatic amine polymer is characterized by one or more repeat units of Structural Formula IX:

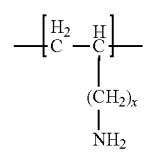

or a pharmaceutically acceptable salt thereof, where x is 0 or an integer between 1 and 4, preferably 1. The polymer represented by Structural Formula IX is advantageously crosslinked by means of a multifunctional cross-linking agent.

Another preferred polymer for use in the invention is polyallylamine, which is a polymer having repeat units from polymerized allyl amine monomers. The amine group of an allyl monomer can be unsubstituted or substituted with, for example, one or two C1-C10 straight chain or branched alkyl groups. The alkyl groups are optionally substituted with one or more hydroxyl, amine, halo, phenyl, amide or nitrile groups. Preferably, the polyallylamine polymers of the present invention comprise repeat units represented by Structural Formula X:

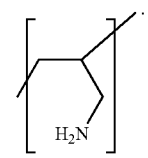

An amine polymer can be a homopolymer or a copolymer of one or more amine-containing monomers or a copolymer of one or more amine-containing monomers in combination with one or more different amine containing monomer or non-amine containing monomers. Copolymers that include one or more repeat units represented by the above Structural Formulas I-X, contain comonomers that are preferably inert and non-toxic. Examples of suitable non-amine-containing monomers include vinyl alcohol, acrylic acid, acrylamide, and vinylformamide.

Also polyallyamine can be a copolymer comprising repeat units from two or more different polymerized allyl monomers or with repeat units from one or more polymerized allyl monomers and repeat units from one or more polymerized non-allyl monomers. Examples of suitable non-allyl monomers include acrylamide monomers, acrylate monomers, maleic acid, malimide monomers, vinyl acylate monomers and alkyl substituted olefines. Preferably, however, the polyallyamines used in the present invention comprise repeat units solely from polymerized allyl amine monomers. More preferably, the polyallyamine polymers used in the present invention are homopolymers. Even more preferably, the polyallyamine polymers used in the present invention are homopolymers of repeat units represented by Structural Formula X or are crosslinked homopolymers thereof.

Preferably, an aliphatic amine polymer is a homopolymer, such as a homopolyallyamine, homopolyvinylamine, homopolydiallyamine or polyethyleneamine. The word "amine," as used herein, includes primary, secondary and tertiary amines, as well as ammonium groups such as trialkylammonium.

Aromatic amine polymers comprise an amine-containing aromatic moiety in one or more of the repeat units. An example of an aromatic amine polymer is poly(aminostyrene).

Amine polymers used in the invention protonated with $H_2CO_3$ or $HCO_3^-$. Preferably, less than 40%, less than 30%, less than 20% or less than 10% of the amine groups are protonated. In another embodiment 10% to 70%, 20% to 60%, 30 to 50% or 35% to 45% of the amines are protonated (e.g., approximately 40%), such as Renagel® which is commercially available from Genzyme Corporation.

The preferred polymers employed in the invention are water-insoluble, non-absorbable, optionally cross-linked polyamines. Preferred polymers are aliphatic. Examples of preferred polymers include polyethyleneimine, polyallylamine, polyvinylamine and polydiallyamine polymers. The polymers can be homopolymers or copolymers, as discussed above, and can be substituted or unsubstituted. These and other polymers which can be used in the claimed invention have been disclosed in U.S. Pat. Nos. 5,487,888; 5,496,545; 5,607,669; 5,618,530; 5,624,963; 5,667,775; 5,679,717; 5,703,188; 5,702,696; 5,693,675; 5,900,475; 5,925,379; 6,083,497; 6,177,478; 6,083,495; 6,203,785; 6,423,754; 6,509,013; 6,556,407; 6,605,270; and 6,733,780 the contents of which are hereby incorporated herein by reference in their entireties. Polymers suitable for use in the invention are also disclosed in U.S. application Ser. No. 08/823,699 (now abandoned); Ser. No. 08/835,857 (now abandoned); Ser. No. 08/470,940 (now abandoned); Ser. No. 08/927,247 (now abandoned); Ser. Nos. 08/964,498; 09/691,429; 10/125,684; 10/158,207; 10/322,904; 10/441,157; and 10/766,638, the contents of which are incorporated herein by reference in their entireties.

Preferably, the polymer is rendered water-insoluble by cross-linking such as with a multifunctional cross-linking agent. The cross-linking agent is typically characterized by functional groups which react with the amino group of the monomer. Alternatively, the cross-linking agent can be characterized by two or more vinyl groups which undergo free radical polymerization with the amine monomer. The degree of polymerization in cross-linked polymers cannot generally be determined.

Examples of suitable multifunctional cross-linking agents include diacrylates and dimethylacrylates (e.g. ethylene glycol diacrylate, propylene glycol diacrylate, butylene glycol diacrylate, ethylene glycol dimethacrylate, propylene glycol dimethacrylate, butylene glycol dimethacrylate, polyethyleneglycol dimethacrylate and polyethyleneglycol diacrylate), methylene bisacrylamide, methylene bismethacrylamide, ethylene bisacrylamide, ethylene bismethacrylamide, ethylidene bisacrylamide, divinylbenzene, bisphenol A, dimethacrylate and bisphenol A diacrylate. The cross-linking agent can also include acryloyl chloride, epichlorohydrin, butanediol diglycidyl ether, ethanediol diglycidyl ether, succinyl dichloride, the diglycidal ether of bisphenol A, pyromellitic dianhydride, toluene diisocyanate, ethylene diamine and dimethyl succinate.

The level of cross-linking renders the polymers insoluble and substantially resistant to absorption and degradation, thereby limiting the activity of the polymer to the gastrointestinal tract, and reducing potential side-effects in the patient. The compositions thus tend to be non-systemic in activity. Typically, the cross-linking agent is present in an amount from about 0.5-35% or about 0.5-25% (such as from about 2.5-20% or about 1-10%) by weight, based upon total weight of monomer plus cross-linking agent.

In some cases the polymers are crosslinked after polymerization. One method of obtaining such crosslinking involves reaction of the polymer with difunctional crosslinkers, such as epichlorohydrin, succinyl dichloride, the diglycidyl ether of bisphenol A, pyromellitic dianhydride, toluence diisocyanate, and ethylenediamine. A typical example is the reaction of poly(ethyleneimine) with epichlorohydrin. In this example the epichlorohydrin (1 to 100 parts) is added to a solution containing polyethyleneimine (100 parts) and heated to promote reaction. Other methods of inducing crosslinking on already polymerized materials include, but are not limited to, exposure to ionizing radiation, ultraviolet radiation, electron beams, radicals, and pyrolysis.

Examples of preferred crosslinking agents include epichlorohydrin, 1,4 butanedioldiglycidyl ether, 1,2 ethanedioldiglycidyl ether, 1,3-dichloropropane, 1,2-dichloroethane, 1,3-dibromopropane, 1,2-dibromoethane, succinyl dichloride, dimethylsuccinate, toluene diisocyanate, acryloyl chloride, and pyromellitic dianhydride. Epichlorohydrin is a preferred crosslinking agent, because of its high availability and low cost. Epichlorohydrin is also advantageous because of its low molecular weight and hydrophilic nature, increasing the water-swellability and gel properties of the polyamine. Epichlorohydrin forms 2-hydroxypropyl crosslinking groups. In a preferred embodiment, the present invention is a polyallyamine polymer crosslinked with epichlorohydrin.

Typically, between about 9% and about 30% of the allylic nitrogen atoms are bonded to a crosslinking group, preferably between 15% and about 21%.

In a preferred embodiment, the polyallyamine polymer used in the present invention is polyallyamine crosslinked with about 9.0-9.8% w/w epichlorohydrin, preferably 9.3-9.5% which is known as sevelamer. The structure is represented below:

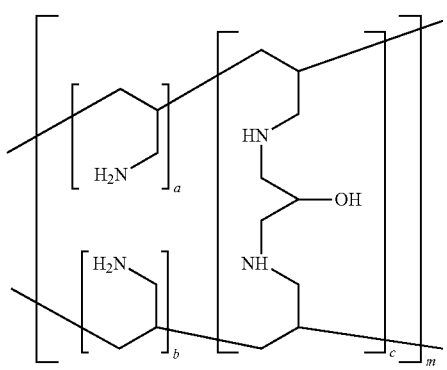

XI where:
the sum of a and b (the number of primary amine groups) is 9;
c (the number of crosslinking groups) is 1;
n (the fraction of protonated amines) is 0.4; and
m is a large number (to indicate extended polymer network).

Typically, the amount of epichlorohydrin is measured as a percentage of the combined weight of polymer and crosslinking agent.

The polymers can also be further derivatized; examples include alkylated amine polymers, as described, for example, in U.S. Pat. Nos. 5,679,717, 5,607,669 and 5,618,530, the teachings of which are incorporated herein by reference in their entireties. Preferred alkylating agents include hydrophobic groups (such as aliphatic hydrophobic groups) and/or quaternary ammonium- or amine-substituted alkyl groups.

Non-cross-linked and cross-linked polyallylamine and polyvinylamine are generally known in the art and are commercially available. Methods for the manufacture of polyallylamine and polyvinylamine, and cross-linked derivatives thereof, are described in the above U.S. Patents. Patents by Harada et al. (U.S. Pat. Nos. 4,605,701 and 4,528,347), which are incorporated herein by reference in their entireties, also describe methods of manufacturing polyallylamine and cross-linked polyallylamine. A patent by Stuns et al. (U.S. Pat. No. 6,180,754) describes an additional method of manufacturing cross-linked polyallylamine.

In other embodiments, the polymer can be a homopolymer or copolymer of polybutenylamine, polylysine, or polyarginine. Alternatively, the polymer can be an aromatic polymer, such as an amine or ammonium-substituted polystyrene, (e.g., cholestyramine).

The molecular weight of polymers of the invention is not believed to be critical, provided that the molecular weight is large enough so that the polymer is non-absorbable by the gastrointestinal tract. Typically the molecular weight is at least 1000. For example the molecular weight can be from: about 1000 to about 5 million, about 1000 to about 3 million, about 1000 to about 2 million or about 1000 to about 1 million.

As described above, the polymers are protonated and are administered in the form of a salt. By "salt" it is meant that the nitrogen group in the repeat unit is protonated to create a positively charged nitrogen atom associated with a negatively charged counterion. Preferably, the salt is a weak acidic salt such as carbonate, bicarbonate, acetate or lactate.

In one embodiment, the present invention is a tablet or composition comprising a carbonate salt of an aliphatic amine polymer and a monovalent anion source, wherein the monovalent anion comprises at least 0.01%, preferably 0.05%, more preferably a range of 0.01% to 2%, 0.05% to 1%, 0.08% to 0.5%, or 0.1% to 0.3% by weight of the combined weights of the carbonate salt and the monovalent anion source.

The monovalent anion is selected to minimize adverse effects on the patient. Examples of suitable anions include organic ions, inorganic ions, or a combination thereof, such as halides ($Cl^-$, $I^-$, $Fl^-$ and $Br^-$), $CH_3OSO_3^-$, $HSO_4^-$, acetate, lactate, butyrate, propionate, sulphate, citrate, tartrate, nitrate, sulfonate, oxalate, succinate or palmoate. Preferred anions are halides, most preferably chloride. The monovalent anion is other than $HCO_3^-$.

In one embodiment, the monovalent anion source is a pharmaceutically acceptable acid, ammonium or metal salt of a monovalent anion. For example, monovalent anion source can be a lithium, sodium, potassium, magnesium, calcium, aluminium, lanthanide, or actinide salt of a monovalent anion. The monovalent anion source can be ammonium, a mono, di, tri or tetra alkylated ammonium. Any of the above described monovalent anions can be combined with any of the metals listed above, of with $H^+$. Preferably the monovalent anion source is sodium chloride or hydrochloric acid. In one embodiment, the tablet or composition comprises a carbonate salt of sevelamer and sodium chloride. In one preferred embodiment, the tablet or composition comprises a carbonate salt of sevelamer and sodium chloride powder. In another preferred embodiment, the tablet or composition comprises a carbonate salt of sevelamer coated with a sodium chloride solution. In yet another embodiment the tablet or composition comprises a carbonate salt of sevelamer and hydrochloric acid.

In the above described embodiment, the monovalent anion, for example, the chloride ions comprise 0.01%, preferably 0.05%, more preferably a range of 0.01% to 2%, 0.05% to 1%, 0.08% to 0.5%, or 0.1% to 0.3% the weight of the carbonate salt of the aliphatic amine polymer plus the weight of the metal salt or acid, for example the weight of sevelamer carbonate plus the weight of sodium chloride.

In another embodiment, the monovalent anion source is a monovalent anion salt of an aliphatic amine polymer comprising a repeat unit represented by Structural Formulas I-XI above. The combination of a carbonate salt of an aliphatic amine polymer and a monovalent anion salt of an aliphatic amine polymer is defined herein as a "physically mixed polymer". The monovalent anion salt of the aliphatic amine polymer can be the same or a different aliphatic amine polymer as the aliphatic amine polymer carbonate salt. Preferably the monovalent anion salt of the aliphatic amine polymer is polyallylamine, more preferably the monovalent anion salt of the aliphatic amine polymer is a homopolymer, most preferably the monovalent anion salt of the aliphatic amine polymer is sevelamer. In a preferred embodiment the monovalent anion source is a halide salt of sevelamer, more preferably sevelamer chloride, (sold under the tradename RENAGEL®). In another preferred embodiment the monovalent anion salt of the aliphatic amine polymer is a chloride salt of sevelamer and the aliphatic amine polymer carbonate salt is sevelamer carbonate.

In the above described embodiment the carbonate salt of the aliphatic amine polymer and the monovalent anion salt of the aliphatic amine polymer are preferably at a molar ratio of 1:2000, 1:500, 1:100, 1:50, 1:20, 1:9, 1:6, 1:4, 1:3, 1:2, or 1:1 monovalent anion:carbonate salt, more preferably at a molar ratio of 1:4 monovalent anion:carbonate salt. In this embodiment, the monovalent anion, for example, the chloride ions, comprise at least 0.01%, preferably 0.05%, more preferably at a range 0.01% to 2%, 0.05% to 1%, 0.08% to 0.5%, or 0.1% to 0.3% by weight of the weight of the carbonate salt of the aliphatic amine polymer plus the weight of the monovalent anion salt of the aliphatic amine polymer, for example, the weight of sevelamer carbonate plus the weight of sevelamer chloride.

In another embodiment the monovalent anion source is the carbonate salt of an aliphatic amine polymer. In this embodiment, the aliphatic amine polymer comprises mainly carbonate ions but also further comprises a monovalent anion other than carbonate. In this embodiment the present invention is a tablet comprising a mixed carbonate and monovalent anion salt of an aliphatic amine polymer. The combination of a carbonate salt and a monovalent anion salt on a single aliphatic amine polymer is defined herein as a "chemically mixed polymer". The aliphatic amine polymer comprises repeat units represented by Structural Formulas I-XI above; preferably the aliphatic amine polymer is sevelamer. Any monovalent anion described above can be used in this embodiment. Preferably the monovalent anion salt is a halide salt, more preferably a chloride salt. Preferably the mixture of carbonate salt to monovalent anion salt is at a molar ratio of monovalent anion:carbonate, of 1:2000, 1:500, 1:100, 1:50, 1:20, 1:4, or 1:1. In this embodiment the monovalent anion, for example, the chloride ions, comprise at least 0.01%, preferably 0.05%, more preferably at a range 0.01% to 2%, 0.05% to 1%, 0.08% to 0.5%, or 0.1% to 0.3% by weight of the weight of the mixed carbonate and monovalent anion salt of the aliphatic amine polymer, for example, the weight of sevelamer with both carbonate and chloride ions.

These chemically mixed polymers can be prepared by adding, for example, aqueous solution of sodium carbonate and/or sodium bicarbonate to an aqueous solution of sevelamer chloride. The ratios of salts to sevelamer chloride may be varied in order to get the desired salt ratio in the chemically mixed polymer. Preferred molar ratios include 1:2000, 1:500, 1:100, 1:50, 1:20, 1:4, or 1:1 sevelamer hydrochloride:carbonate.

In another embodiment, the chemically mixed aliphatic amine polymer may be mixed with a carbonate salt of an aliphatic amine polymer. The aliphatic amine polymers comprise repeat units represented by Structural Formulas I-XI above and may be the same or different. Preferably the chemically mixed polymer and the carbonate salt polymer are sevelamer. The preferred anions on the chemically mixed polymer are as described above. Preferably the chemically mixed polymer and carbonate polymer are at a molar ratio of chemically mixed salt:carbonate, of 1:2000, 1:500, 1:100, 1:50, 1:20, 1:4, or 1:1.

Increasing the particle size of the aliphatic amine polymer particles results in an increase in shelf life of the tablets of the present invention and prevents the disintegration time of the tablets from increasing over time. The particles comprise of an aliphatic amine polymer, preferably polyallyamine polymer, more preferably a homopolymer, most preferably sevelamer, and optionally one or more additional pharmaceutically acceptable ingredients. In a preferred embodiment the particles comprise at least 80%, preferably at least 90% more preferably at least 95%, most preferably at least 100%, by weight of aliphatic amine polymer.

In one embodiment, the present invention is a tablet comprising particles of a carbonate salt of aliphatic amine polymer, preferably polyallyamine polymer, more preferably sevelamer, most preferably sevelamer carbonate, wherein at least 95% by volume of the particles have a diameter of at least 45 microns, at least 60 microns, at least 80 microns or at least 100 microns.

These aliphatic amine polymer particles may be combined with for example, an excipient, carrier or diluent, to form the tablets or compositions of the present invention.

The tablets of the present invention can comprise one or more excipients, such as binders, glidants and lubricants, which are well known in the art. Suitable excipients include colloidal silicon dioxide, stearic acid, magnesium silicate, calcium silicate, sucrose, cellulose, calcium stearate, glyceryl behenate, magnesium stearate, talc, zinc stearate and sodium stearylfumarate, a cellulose derivative such as carboxymethyl cellulose, microcrystalline cellulose, hydroxypropyl cellulose, acacia, tragacanth, pectin, gelatin, polyethylene glycol. Preferably the cellulose derivative is microcrystalline cellulose, more preferably Ceolus® (Asahi Kasei Chemicals Corporation).

The tablets of the invention are prepared by a method comprising the steps of:
(1) hydrating or drying the aliphatic amine polymer to the desired moisture level;
(2) blending the aliphatic amine polymer with any excipients to be included; and
(3) compressing the blend using conventional tableting technology.

The tablet is optionally coated, i.e., the aliphatic amine polymer and excipients form a core surrounded by a coating. In one embodiment, the coating composition comprises a cellulose derivative and a plasticizing agent. The cellulose derivative is, preferably, hydroxypropylmethylcellulose (HPMC). The cellulose derivative can be present as an aqueous solution. Suitable hydroxypropylmethylcellulose solutions include those containing HPMC low viscosity and/or HPMC high viscosity. Additional suitable cellulose derivatives include cellulose ethers useful in film coating formulations. The plasticizing agent can be, for example, an acetylated monoglyceride such as diacetylated monoglyceride, The coating composition can further include a pigment selected to provide a tablet coating of the desired color. For example, to produce a white coating, a white pigment can be selected, such as titanium dioxide.

In one embodiment, the coated tablet of the invention can be prepared by a method comprising the step of contacting a tablet core of the invention, as described above, with a coating solution comprising a solvent, at least one coating agent dissolved or suspended in the solvent and, optionally, one or more plasticizing agents. Preferably, the solvent is an aqueous solvent, such as water or an aqueous buffer, or a mixed aqueous/organic solvent. Preferred coating agents include cellulose derivatives, such as hydroxypropylmethylcellulose. Typically, the tablet core is contacted with the coating solution until the weight of the tablet core has increased by an amount ranging from about 3% to about 6%, indicating the deposition of a suitable coating on the tablet core to form a coated tablet.

In one preferred embodiment, the solids composition of the coating solution is:

| Material | % W/W |
|---|---|
| HPMC low viscosity Type 2910, cUSP | 38.5% |
| HPMC high viscosity Type 2910, cUSP | 38.5% |
| diacetylated monoglyceride | 23.0% |

Tablets may be coated in a rotary pan coater as is known in the art or any other conventional coating apparatus such as a column coater or a continuous coater.

The present invention also encompasses pharmaceutical compositions other than tablets. These pharmaceutical compositions comprise a pharmaceutically acceptable carrier or diluent and a carbonate salt of an aliphatic amine polymer and a monovalent anion source as described above. Preferably the monovalent anion source comprises at least 0.01%, preferably 0.05%, more preferably at a range 0.01% to 2%, 0.05% to 1%, 0.08% to 0.5%, or 0.1% to 0.3% by weight of the combined weight of the carbonate salt and the monovalent anion source.

The aliphatic amine polymers, tablets and compositions of the present invention are preferably administered orally. They can be administered to the subject alone or in a pharmaceutical composition, and optionally, one or more additional drugs. The pharmaceutical compositions of the invention preferably contain a pharmaceutically acceptable carrier or diluent suitable for rendering the compound or mixture administrable orally. The active ingredients may be admixed or compounded with a conventional, pharmaceutically acceptable carrier or diluent. It will be understood by those skilled in the art that any mode of administration, vehicle or carrier conventionally employed and which is inert with respect to the active agent may be utilized for preparing and administering the pharmaceutical compositions of the present invention. Illustrative of such methods, vehicles and carriers are those described, for example, in Remington's Pharmaceutical Sciences, 18th ed. (1990), the disclosure of which is incorporated herein by reference.

The formulations of the present invention for use in a subject comprise the agent, together with one or more acceptable carriers or diluents therefore and optionally other therapeutic ingredients. The carriers or diluents must be "acceptable" in the sense of being compatible with the other ingredients of the formulation and not deleterious to the recipient thereof. The formulations can conveniently be presented in unit dosage form and can be prepared by any of the methods well known in the art of pharmacy. All methods include the step of bringing into association the agent with the carrier or diluent which constitutes one or more accessory ingredients. In general, the formulations are prepared by uniformly and intimately bringing into association the agent with the carriers and then, if necessary, dividing the product into unit dosages thereof.

Those skilled in the art will be aware that the amounts of the various components of the compositions of the invention to be administered in accordance with the method of the invention to a subject will depend upon those factors noted above.

The compositions of the invention can be formulated as a tablet, sachet, slurry, food formulation, troche, capsule, elixir, suspension, syrup, wafer, chewing gum or lozenge. A syrup formulation will generally consist of a suspension or solution of the compound or salt in a liquid carrier, for example, ethanol, glycerine or water, with a flavoring or coloring agent. Where the composition is in the form of a tablet, one or more pharmaceutical carriers routinely used for preparing solid formulations can be employed. Examples of such carriers include magnesium stearate, starch, lactose and sucrose. Where the composition is in the form of a capsule, the use of routine encapsulation is generally suitable, for example, using the aforementioned carriers in a hard gelatin capsule shell. Where the composition is in the form of a soft gelatin shell capsule, pharmaceutical carriers routinely used for preparing dispersions or suspensions can be considered, for example, aqueous gums, celluloses, silicates or oils, and are incorporated in a soft gelatin capsule shell.

The aliphatic amine polymers, tablets and compositions can be administered as multiple dosage units or as a single dosage unit. As used herein a dosage unit may be a tablet, sachet, slurry, food formulation, troche, capsule, elixir, suspension, syrup, wafer, chewing gum or the like prepared by art recognized procedures. Preferably a dosage unit is a tablet, capsule, sachet, slurry, suspension or food formulation, more preferably the dosage unit is a tablet, slurry, suspension or food formulation, most preferably the dosage unit is a tablet or sachet. Typically, the desired dose of an aliphatic amine polymer is administered as multiple tablets or capsules, or a single dose of a sachet, slurry, food formulation, suspension or syrup.

In one example, the dosage unit is an oval, film coated, compressed tablet containing either 800 mg or 400 mg of sevelamer on an anhydrous basis. The inactive ingredients are sodium chloride, zinc stearate, Ceolus®, hypromellose, and diacetylated monoglyceride. In yet another embodiment, the dosage unit is a hard-gelatin capsule containing 403 mg of sevelamer on an anhydrous basis. The inactive ingredients are sodium chloride, zinc stearate, Ceolus®, hypromellose, and diacetylated monoglyceride.

The aliphatic amine polymers, tablets and compositions of the present invention are preferably administered with meals.

The methods of the invention involve treatment of patients with hyperphosphatemia. Elevated serum phosphate is commonly present in patients with renal insufficiency, hypoparathyroidism, pseudohypoparathyroidism, acute untreated acromegaly, overmedication with phosphate salts, and acute tissue destruction as occurs during rhabdomyolysis and treatment of malignancies.

As used herein a subject is a mammal, preferably a human, but can also be an animal in need of veterinary treatment, such as a companion animal (e.g., dogs, cats, and the like), a farm animal (e.g., cows, sheep, pigs, horses, and the like) or a laboratory animal (e.g., rats, mice, guinea pigs, and the like).

A therapeutically effective amount of compound is that amount which produces a result or exerts an influence on the particular condition being treated. As used herein, a therapeutically effective amount of a phosphate binder means an amount which is effective in decreasing the serum phosphate levels of the patient to which it is administered.

Typical dosages of phosphate binders range from about 5 milligrams/day to about 10 grams/day, preferably from about 50 milligrams/day to about 9 grams/day, more preferably from about 1 gram/day to about 8 grams/day, even more preferably about 2 grams to about 7 grams, most preferably about 4 grams/day to about 6 grams/day. The phosphate binders of the present invention can be administered at least four times per day with meals, at least three times per day with meals, at least twice per day with meals, at least once per day with meals, (see U.S. Provisional Application No. 60/623, 985 the entire contents of which are incorporated herein by reference).

EXEMPLIFICATION

Example 1

Better compactability and disintegration time of mixed aliphatic amine carbonate salt and monovalent anion formulation as compared to the formulation containing sevelamer carbonate alone.

The term "physically mixed salt" refers to dry blending of sevelamer HCl and sevelamer carbonate API (2 compounds). The total chloride was targeted to be in the range of 4 to 6%.

Based on the ratios of sevelamer hydrochloride to sevelamer carbonate used, the % LOD for the final mixture of sevelamer hydrochloride and sevelamer carbonate was calculated. For the wetting of the mixture to target % loss on drying (LOD), the sevelamer hydrochloride API, sevelamer carbonate API and Ceolus® were added directly to the Diosna (a high shear wetting equipment/granulator). The blend was mixed for 3 minutes using the impeller rotating at 435 rpm. Purified water was then added to the blend using a spray bottle to achieve the target LOD in a Diosna Granulator over a 20 minute mixing period. The blend was mixed for an additional 3 minutes at an impeller speed of 435 rpm. The blend was transferred from the Diosna bowl to a double lined plastic bag that was then securely closed and stored in a plastic container. The wetted blend was allowed to equilibrate for 24 hours.

After 24 hours, the required quantities of wetted material and lubricant were weighed. The wetted material was screened using a co-mill fitted with a 600-micron screen with the impeller rotating at 2500 rpm. A portion of wetted blend was bag-blended with appropriate lubricant, passed through a 600-micron screen and a second portion of wetted sevelamer was passed through the 600-micron screen. The wetted blend and lubricant were then blended in a V-blender for 115 revolutions.

The powder blend was compressed into tablets using a rotary tablet press (Jenn-Chiang Machinery Co. Ltd., (JC-MCO)) adjusted to meet the target weight and hardness. The press was set up with 1 station of B press tooling which has the same surface area as the commercial tooling (0.405'×0.748"). The tablets were compressed using different compression parameters. An average compactibility (ratio of tablet hardness over the main compression force used on the tablet press) was determined from these conditions. The tablets were dedusted. This process was generally done at 0.5 to 1.5 kg scale.

The disintegration testing of the tablets was performed in simulated gastric fluid USP without enzymes having a pH of 1.2 (0.1N HCl). The details of the disintegration apparatus and procedure followed are described below.

Disintegration Testing Apparatus (USP27/NF22):

The apparatus consisted of a basket-rack assembly, a 1000-ml beaker, a thermostatic arrangement for heating the fluid between 35° C. and 39° C., and a device for raising and lowering the basket in the immersion fluid at a constant frequency rate 25, between 29 and 32 cycles per minute.

The basket-rack assembly consisted of six open-ended transparent tubes. The tubes were held in a vertical position by two plastic plates with six holes equidistant from the center of the plate and equally spaced from one another. Attached to the under surface of the lower plate was a woven stainless steel wire cloth which had plain square weave with 1.8 to 2.2 mm mesh apertures and with a wire diameter of 0.63±0.03 mm. A 10-mesh screen was also put on the top of the basket to avoid the tablet from coming out during the disintegration testing. A suitable means was provided to suspend the basket-rack assembly from the raising and lowering device using a point on its axis.

Testing Procedure:

The simulated gastric fluid USP without enzymes having a pH of 1.2 (0.1N HCl) (900 ml) was placed in the 1000 ml beaker and heated to 37° C. using the water bath of the disintegration apparatus. Two tablets were tested by putting each one in separate tubes of the basket-rack assembly and a 10 mesh screen was placed on the top to prevent the tablets from coming out. The lowering and raising device was turned on and the tablets were observed for the rupture time (i.e. the time when the coating on the tablet first ruptures and polymer starts coming out) and disintegration time (i.e. the time when the tablet disintegrates completely and comes out from the tube of the basket-rack assembly).

The physically mixed salt formulations containing sevelamer hydrochloride and sevelamer carbonate Active Pharmaceutical Ingredient (API) were evaluated. The data suggested that physically mixed salt formulation had better compactability and disintegration time as compared to the formulation containing sevelamer carbonate API only (see Table 1). The disintegration time for the tablets manufactured using the physically mixed salt approach was significantly faster as compared to the formulation containing sevelamer carbonate API only.

TABLE 1

Comparison of sevelamer carbonate vs physical mixture approaches

| Approach | % LOD | % Ceolus | % CSD | Lubricant used | % Lubricant | Sevelamer hydrochloride lot # | Sevelamer carbonate lot # | Sev. HCl: Sev. CO3 wt. Ratio | Hardness (N) | Average t = 0 | Average 1 week | Average 2 weeks | Average 3 weeks |
|---|---|---|---|---|---|---|---|---|---|---|---|---|---|
| Sevelamer Carbonate only | 10.5 | 14 | 0.25 | Glyceryl dibehenate | 1.2 | NA | 2416344 | NA | 431 | 3.2 | 32.4 | 34.6 | 36.8 |
| Physically mixed | 8 | 0 | 0.375 | Stearic acid | 0.4 | 2448260 | 2416344 | 1 to 3 | 386 | 2.5 | 2.7 | 2.4 | 2.4 |
|  |  |  |  |  |  |  |  |  | 327 | ND | ND | ND | ND |
| Physically mixed | 8 | 0 | 0.375 | Stearic acid | 0.4 | 2448260 | 2416344 | 1 to 6 | 98 | 1.7 | ND | 0.7 | 1.4 |
|  | 8 | 0 | 0.375 | Stearic acid | 0.4 | 2448260 | 2416344 | 1 to 9 | 90 | 2.3 | ND | ND | 2.2 |

The above results show that the physically mixed salt formulation can provide desirable compactability and the disintegration times remain more stable over time compared to formulation containing sevelamer carbonate only.

Example 2

Effect of various ratios of sevelamer HCl to sevelamer carbonate on compactability, ejection forces and disintegration times.

The sevelamer hydrochloride to sevelamer carbonate ratios of 1:1, 1:3, 1:6 and 1:9 were evaluated using the excipients used in the Renagel® formulation (800 mg active API, 8% target LOD, 0.375% colloidal silicon dioxide and 0.4% stearic acid) (see Table 2). All experiments were carried out as described above for Example 1

TABLE 2

Effect of various ratios of sevelamer HCl to sevelamer carbonate on disintegration times.

| Sev. HCl: Sev. CO3 wt. Ratio | PC (kN) | CF- (kN) | Compactibility (N/kN) | Disintegration Time (minutes) of Core Tablets stored at 60 C. Performed in pH 1.2 with disk and screen | | | |
|---|---|---|---|---|---|---|---|
| | | | | Average t = 0 | Average 1 week | Average 2 weeks | Average 3 weeks |
| 1 to 1 | 15 | 19 | 15.9 | 0.8 | 1.9 | 1.3 | 1.3 |
| 1 to 3 | 15 | 44 | 8.7 | 2.5 | 2.7 | 2.4 | 2.4 |
| 1 to 6 | 15 | 45 | 2.2 | 1.7 | ND | 0.7 | 1.4 |
| 1 to 9 | 15 | 45 | 2.0 | 2.3 | ND | ND | 2.2 |

Formulation: 8% LOD, No Ceolus, 0.375% Colloidal silicon dioxide (CSD), 0.4% stearic acid
ND: Not determined, PC: Precompression force; CF: Compression Force;
Disintegration testing, n = 2

Based on the above studies, it can be seen that the disintegration time is maintained in a pharmaceutically acceptable range with all the ratios of chloride to carbonate salts evaluated. salt also resulted in pharmaceutically acceptable disintegration times.

Example 3

Comparison of Physically Mixed Salts with Chemically Mixed Salts

All experiments were carried out as described above for Example 1. As can be seen from Table 3 the chemically mixed salt were prepared by adding sevelamer hydrochloride to an aqueous solution of sodium carbonate and sodium bicarbonate.

TABLE 3

Comparison of physically mixed and chemically mixed salt

| Approach | % LOD | % Ceolus | Lubricant used | % Lubricant | Sevelamer hydrochloride lot # | Sevelamer carbonate lot # | % Chloride | Hardness (N) | Disintegration Time (minutes) of Core Tablets stored at 60 C. Performed in pH 1.2 with disk and screen | | | |
|---|---|---|---|---|---|---|---|---|---|---|---|---|
| | | | | | | | | | Average t = 0 | Average 1 week | Average 2 weeks | Average 3 weeks |
| Physically mixed | 10.5 | 5 | PRUV | 0.5 | 2448260 | 2416344 | 4 | 488 | 1.1 | 2.4 | 2.8 | 3.3 |
| Chemically mixed | 10.5 | 5 | PRUV | 0.5 | NA | NA | 5 | 305 | 12.1 | 11.3 | 11.2 | 11.5 |
| Physically mixed | 10.5 | 5 | Zinc stearate | 0.5 | 2448260 | 2416344 | 4 | 488 | 1.0 | 4.4 | 4.9 | 5.2 |
| Chemically mixed | 10.5 | 5 | Zinc stearate | 0.5 | NA | NA | 3 | 116 | 7.1 | 6.7 | 6 | 6.2 |

Example 4

Comparison of sevelamer carbonate with sodium chloride and without sodium chloride All experiments were carried out as described above for Example 1. As can be seen from Table 4 the disintegration time increased much more in the case for sevelamer carbonate without sodium chloride,

TABLE 4

Comparison of sevelamer carbonate with sodium chloride and without sodium chloride

| Approach | % LOD | % Ceolus | Lubricant used | Sevelamer carbonate lot # | Hardness (N) | Disintegration Time (minutes) of Core Tablets stored at 60 C. Performed in pH 1.2 with disk and screen | | | |
|---|---|---|---|---|---|---|---|---|---|
| | | | | | | Average t = 0 | Average 1 week | Average 2 weeks | Average 3 weeks |
| No sodium chloride | 10.5 | 14 | Sodium stearyl fumerate | 2416570 | 194 | 2.7 | 24.2 | ND | 29.5 |
| 0.25% Sodium chloride | 10.5 | 15 | Sodium stearyl fumerate | 2416344 | 352 | 3.9 | 8.8 | 9.4 | 13.4 |

From the above studies, it was determined that addition of sodium chloride to sevelamer carbonate significantly decreases the increase in the disintegration time.

Example 5

Effect of Particle Size Cut on the Disintegration Behavior and Compactability

Different particle sizes were compared for the effect on compactability and disintegration time using a formulation of: 6.5% LOD ("as is" API moisture), 25% Ceolus® KG 802, 1.2% Glyceryl dibehenate, No Colloidal silicon dioxide (CSD), (API: 20% carbonate). All experiments were carried out as in Example 1. The compression conditions were: pre-compression force: 151N, compression force: 451 (N, and speed: 20 rpm. The results can be seen in Table 5.

TABLE 5

Effect of particle size cut on the disintegration behavior and compactibility.

| Lab notebook number | Particle size cuts (micron) | Ejection force (N) | Compact (N/kN) | Disintegration time (minutes) of core tablets stored at 60 C. Performed in pH 1.2 with disc and screen | | | |
|---|---|---|---|---|---|---|---|
| | | | | Average t = 0 | Average 1 week | Average 2 weeks | Average 3 weeks |
| 0495-200 | "As is" API | 316 | 8.2 | 2.6 | 12.6 | 15.0 | 15.0 |
| 0484-170 | >53 | 326 | 8.2 | 1.9 | ND | 6.3 | 7.2 |
| 0484-171 | >75 | 316 | 6.9 | 1.8 | ND | 5.5 | 6.2 |
| 0484-172 | >90 | 320 | 6.3 | 1.5 | ND | 4.9 | 5.5 |
| 0484-138 | >106 | 330 | 5.8 | 1.0 | 4.4 | 5.2 | 4.5 |

The above results show that the formulations with increased particle sizes maintain a more stable disintegration time over time compared to formulations with smaller particles sizes.

While this invention has been particularly shown and described with references to preferred embodiments thereof, it will be understood by those skilled in the art that various changes in form and details may be made therein without departing from the scope of the invention encompassed by the appended claims.

What is claimed is:

1. A tablet, comprising:
a tablet core having a length and a width and the largest dimension of the tablet core is about 0.748 inches, wherein the table core comprises:
i) sevelamer carbonate; and
ii) sodium chloride, wherein the chloride of the sodium chloride is present in a range of between 0.1 to 1% by weight relative to the combined weights of the sevelamer carbonate and the sodium chloride.

2. The tablet of claim 1, wherein the tablet core diameter is no greater than 0.748 inches.

3. The tablet of claim 1, wherein the tablet core diameter is 0.748 inches.

4. The tablet of claim 1, wherein the sodium chloride is sodium chloride powder.

5. The tablet of claim 1, wherein the chloride is present in a range of between 0.1 to 0.3% by weight relative to the combined weights of the sevelamer carbonate and the sodium chloride.

6. The tablet of claim 1, further comprising one or more excipients.

7. The tablet of claim 6, wherein the one or more excipients are selected from the group consisting of: colloidal silicon dioxide, stearic acid, magnesium silicate, calcium silicate, sucrose, cellulose, calcium stearate, glyceryl behenate, magnesium stearate, talc, zinc stearate, sodium stearylfumarate, carboxymethyl cellulose, microcrystalline cellulose, hydroxypropyl cellulose, acacia, tragacanth, pectin, gelatin, and polyethylene glycol.

8. The tablet of claim 6, wherein the one or more excipients includes hypromellose.

9. The tablet of claim 6, wherein the one or more excipients includes diacetylated monoglyceride.

10. The tablet of claim 1, wherein the tablet is coated with a coating composition.

11. The tablet of claim 10, wherein the coating composition comprises hydroxypropylmethylcellulose.

12. The tablet of claim 10, wherein the coating composition further comprises a plasticizing agent.

13. The tablet of claim 1, wherein the tablet is an oval, film coated, compressed tablet.

14. The tablet of claim 13, wherein the tablet comprises 800 mg of sevelamer carbonate on an anhydrous basis.

15. The tablet of claim 13, wherein the tablet comprises 400 mg of sevelamer carbonate on an anhydrous basis.

16. A coated tablet, comprising:
i) a coating composition; and
ii) a tablet core having a length and a width and the largest dimension of the tablet core is about 0.748 inches, wherein the table core comprises:
a) sevelamer carbonate; and
b) sodium chloride, wherein the chloride of the sodium chloride is present in a range of between 0.1 to 1% by weight relative to the combined weights of the sevelamer carbonate and the sodium chloride.

17. The coated tablet of claim 16, wherein the tablet core diameter is no greater than 0.748 inches.

18. The coated tablet of claim 16, wherein the tablet core diameter is 0.748 inches.

19. The coated tablet of claim 16, wherein the coating composition comprises an amount ranging from about 3% to about 6% by weight, relative to the weight of the tablet core.

20. The coated tablet of claim 16, further comprising one or more excipients.

21. The tablet of claim 20, wherein the one or more excipients are selected from the group consisting of: colloidal silicon dioxide, stearic acid, magnesium silicate, calcium silicate, sucrose, cellulose, calcium stearate, glyceryl behenate, magnesium stearate, talc, zinc stearate, sodium stearylfumarate, carboxymethyl cellulose, microcrystalline cellulose, hydroxypropyl cellulose, acacia, tragacanth, pectin, gelatin, and polyethylene glycol.

22. The coated tablet of claim 16, wherein the one or more excipients includes diacetylated monoglyceride.

23. The coated tablet of claim 20, wherein the coated tablet comprises 800 mg of sevelamer carbonate on an anhydrous basis.

24. The coated tablet of claim 20, wherein the coated tablet comprises 400 mg of sevelamer carbonate on an anhydrous basis.

* * * * *

UNITED STATES PATENT AND TRADEMARK OFFICE
CERTIFICATE OF CORRECTION

PATENT NO.        : 8,808,738 B2
APPLICATION NO.   : 13/183079
DATED             : August 19, 2014
INVENTOR(S)       : Hitesh R. Bhagat et al.

It is certified that error appears in the above-identified patent and that said Letters Patent is hereby corrected as shown below:

On the Title Page, Item 56
On page 3, in column 2, under "Other Publications", line 2, delete "(sulfon-" and insert -- (sulfone- --, therefor.
On page 3, in column 2, under "Other Publications", line 21, delete "(propul" and insert -- (propyl --, therefor.
On page 3, in column 2, under "Other Publications", line 32, delete "Crosslnker" and insert -- Crosslinker --, therefor.
On page 3, in column 2, under "Other Publications", line 34, delete "Ditribution" and insert -- Distribution --, therefor.
On page 3, in column 2, under "Other Publications", line 51, delete "Analgous" and insert -- Analogous --, therefor.
On page 4, in column 1, under "Other Publications", line 32, delete "crosslined" and insert -- crosslinked --, therefor.
On page 4, in column 2, under "Other Publications", line 8, delete "epichlorahydrin" and insert -- epichlorohydrin --, therefor.
On page 4, in column 2, under "Other Publications", line 8, delete "allyamine,"" and insert -- allylamine," --, therefor.
On page 4, in column 2, under "Other Publications", line 23, delete "Distintegration" and insert -- Disintegration --, therefor.

In the Specification
In column 4, line 30, delete "guanadine," and insert -- guanidine, --, therefor.
In column 5, line 15, delete "malimide" and insert -- maleimide --, therefor.
In column 6, line 19, delete "diglycidal" and insert -- diglycidyl --, therefor.
In column 6, line 37, delete "toluence" and insert -- toluene --, therefor.
In column 7, line 43, delete "Stuns" and insert -- Stutts --, therefor.
In column 9, line 54, delete "polyallyamine" and insert -- polyallylamine --, therefor.
In column 9, line 63, delete "polyallyamine" and insert -- polyallylamine --, therefor.
In column 10, line 37, delete "monoglyceride," and insert -- monoglyceride. --, therefor.

Signed and Sealed this
Twelfth Day of May, 2015

Michelle K. Lee
*Director of the United States Patent and Trademark Office*

CERTIFICATE OF CORRECTION (continued)
U.S. Pat. No. 8,808,738 B2

In column 13, line 62, after "rate" delete "25,".
In columns 13-14, line 3, in Table 1, delete "Perfomed" and insert -- Performed --, therefor.
In column 14, line 67, delete "Example 1" and insert -- Example 1. --, therefor.
In column 16, line 52, delete "chloride," and insert -- chloride. --, therefor.
In columns 15-16, line 8, in Table 4, delete "fumerate" and insert -- fumarate --, therefor.
In columns 15-16, line 10, in Table 4, delete "fumerate" and insert -- fumarate --, therefor.
In column 17, line 16, delete "151N," and insert -- 15kN, --, therefor.
In column 17, line 16, delete "451 (N," and insert -- 45kN, --, therefor.

In the Claims
In column 17, line 50, in claim 1, delete "table" and insert -- tablet --, therefor.
In column 18, line 47, in claim 16, delete "table" and insert -- tablet --, therefor.
In column 18, line 63, in claim 21, delete "tablet" and insert -- coated tablet --, therefor.